United States Patent [19]

Revici

[11] 4,416,869

[45] Nov. 22, 1983

[54] METHOD FOR ELIMINATING OR REDUCING THE DESIRE FOR SMOKING

[75] Inventor: Emanuel Revici, New York, N.Y.

[73] Assignee: The Vinoxen Company, New York, N.Y.

[21] Appl. No.: 323,634

[22] Filed: Nov. 20, 1981

Related U.S. Application Data

[63] Continuation of Ser. No. 74,455, Sep. 11, 1979, abandoned, which is a continuation of Ser. No. 923,657, Jul. 11, 1978, abandoned, which is a continuation of Ser. No. 724,366, Sep. 17, 1976, abandoned, which is a continuation-in-part of Ser. No. 615,207, Sep. 22, 1975, abandoned.

[51] Int. Cl.³ .................... A61K 31/20; A61K 31/23; A61K 33/04
[52] U.S. Cl. .................................. 424/164; 424/127; 424/171; 424/312; 424/318; 424/335
[58] Field of Search ............... 424/164, 171, 312, 318, 424/335, 127

[56] References Cited

U.S. PATENT DOCUMENTS

| | | | |
|---|---|---|---|
| 525,784 | 9/1894 | Helmers | 424/335 |
| 1,995,776 | 3/1935 | Nitardy et al. | 424/171 |
| 2,432,797 | 12/1947 | Peters et al. | 424/335 |

OTHER PUBLICATIONS

Provost, J. Am. Pharm. Assoc. NS4(7) 339, 342-343 (1964).
Revici, Research in Physiopathology as Basis of Guided Chemotherapy (1961) pp. 334-335, p. 711 & Note 7.
Mechanisms of Sulfur Reactions (1962) pp. 42-65.
The Reaction of Sulfur with Olefin, to Produce Organic Sulfides and Polysulfides (1962) pp. 97-116.

*Primary Examiner*—Allen J. Robinson
*Attorney, Agent, or Firm*—Millen & White

[57] ABSTRACT

The invention relates to a method of preventing or reducing the desire for smoking tobacco in humans by the internal administration of a composition produced by heating certain allylically unsaturated compounds sufficient to substantially increase the peroxide titer. The incorporation of sulfur in the composition during the heating has been found to be particularly advantageous.

15 Claims, No Drawings

METHOD FOR ELIMINATING OR REDUCING THE DESIRE FOR SMOKING

CROSS REFERENCE TO RELATED APPLICATIONS

This is a continuation of application Ser. No. 074,455, field Sept. 11, 1979, which is a continuation of application Ser. No. 923,657, filed July 11, 1978, which was a continuation of application Ser. No. 724,366, filed Sept. 17, 1976, which in turn was a continuation-in-part of application Ser. No. 615,207, filed Sept. 22, 1975, all now abandoned.

BACKGROUND OF THE INVENTION

Sulfurized polyunsaturated oils, or sulfurized oils, are disclosed in a book entitled RESEARCH IN PHYSIOPATHOLOGY AS BASIS OF GUIDED CHEMOTHERAPY by Emanual Revici, M.D., published by D. Van Nostrand Company, Inc., 1961, pages 334 and 335. A method of preparing sulfurized polyunsaturated oils referred to in the book as hydropersulfides is set forth in Note 7, page 711 of the book. This book does not disclose the use of the sulfurized compounds for preventing or reducing the desire for smoking tobacco claimed herein.

SUMMARY OF THE INVENTION

The invention relates to a method of eliminating or reducing the desire for smoking tobacco in humans by the internal administration of a composition produced by heating certain allylically unsaturated compounds in the presence of oxygen sufficient to substantially increase the peroxide titer. The incorporation of sulfur into the composition during or before the heating of the compositions has been found to be particularly advantageous and represents the most effective composition found to date. The compositions can be administered to the patient by the various accepted methods such as by injection or preferably orally in capsule form.

DETAILED DESCRIPTION OF THE INVENTION

It is desirable to have a method for treating or aiding in the treatment of the tobacco habit or addiction in a human by controlling the craving for tobacco and/or by controlling withdrawal symptoms.

This invention relates to such methods of treatment involving the internal administration to a human host of a composition produced by oxidizing a fatty acid or fatty ester, for example, by bubbling air through the reaction mixture, structurally characterized by allylic unsaturation alone. The fatty acid or ester advantageously includes elemental sulfur and/or a conventional free radical initiator such as tertiarybutyl peroxide during the heating step.

The allylically unsaturated compound is preferably a naturally occurring fatty ester such as an animal, vegetable, or fish oil. Sesame oil is a vegetable oil consisting largely of triglycerides and is the most advantageous composition found to date in the practice of this invention.

The composition utilized preferably should contain a significant percentage of allylic moieties (to render the compositions useful according to the invention) indicated by the following partial structures

and/or

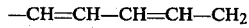

As indicated, the unsaturation can be conjugated or nonconjugated but the composition must contain allylic methylene hydrogen.

Such compositions, as the case may be, should be oxidized or heated in the presence of oxygen at a temperature in the range between about 110° C. and about 150° C. The oxygen can be obtained by merely heating the composition open to the atmosphere but preferably and advantageously, the source of oxygen is a gas such as air injected into a heated oil such as sesame oil. The injected air also serves as a source of agitation.

As previously stated it is most advantageous to add elemental sulfur such as sublimed, precipitated, or washed sulfur to the compositions so that the sulfur is present with oxygen during at least a portion of the heating period and the sulfur incorporated into the composition. Additionally, a previous batch of the oxidized oil with or without sulfur or tert-butyl peroxide may advantageously be present during at least a portion of the heating period.

If sulfur is added to the selected composition, for example, sesame oil, the temperature should be maintained at an upper limit within the range of about 120° C. to about 130° C., and preferably 125° C. and 127° C. These temperature limitations are based on a heating time of about one-half hour. The temperatures can be altered within limits depending on the time of heating. For example, the temperature can be 129°–130° C. if the time is shorter or even at 140° C. for very short period of time. High temperatures for a prolonged period of time tend to degrade the composition and should thus be avoided.

If sulfur is not present during the heating period, the temperature should be maintained in the range between about 110° C. and about 150° C., and preferably in the range between about 120° C. and about 140° C.

The heat treatment is conducted for a period of from about 15 minutes to about two hours. If sulfur is present, optimal results are obtained if the heat treatment is conducted for a period of time between about 30 minutes to about 1 hour. If a free radical initiator is present, or if a selected composition inherently contains a significant amount of initiator, the heat treatment period may be conducted for a relatively shorter period of time.

The precise nature of the composition which results from the above-described treatment or the identity of the effective component or components is not presently known to the applicant. However, while applicant does not wish his invention limited by the following theory or fact, or mixed theory and fact as the case may be, certain evidence in available which indicates that an efficacious composition for the preventing or reducing the desire for tobacco in a human can be produced according to this invention.

In particular, it appears that a correlation exists between a composition useful for the subject purpose and its presumed peroxide or hydroperoxide content. By adhering to the process according to this invention, it has been found that efficacious compositions are produced which yield a significant peroxide titer when monitored by conventional iodometric analysis, the results being expressed, for example, in terms of microequivalents per gram. By significant peroxide titer is meant a value obtained which is greater than that which inherently may be present in the initial untreated compound.

In the case of triglycerides which contain the allylic type unsaturation as described above, the resulting oxidized species is thought to be a hydroperoxide represented by the following partial structure

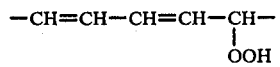

as interpreted via UV spectroscopic analysis, inter alia.

Whatever the nature of the oxidized species, it appears amenable to monitoring by conventional iodometric analysis with or without the addition of sulfur.

Although it appears that the activity of the composition is coincident with the presence of peroxides or hydroperoxides, the efficacious agent need not necessarily be directly derived from these classes. It may in fact be those species derived from radicals resulting from decomposition of compounds of, for example, triglyceride oils or sulfur including olefinic polymerization products and/or lower molecular weight decomposition products of the oils or additional products with sulfur such as sulfides, disulfides, hydropersulfides, etc.

With regard to a preferred embodiment, it appears that the presence of elemental sulfur (approximately 1% by weight based on sesame seed oil) during the oxidation of sesame oil increase the amounts of oxidation products (conjugated hydroperoxides, diene, triene, unsaturated carbonyl) and that this increase appears optimal near 127° C. as evidenced by UV spectroscopic analysis studies. In the absence of sulfur, it appears that the region near 127° C. is optimal for the production of oxidation products.

As mentioned above, it appears that the most effective compositions are those which have a relatively high peroxide titer. Comparisons of a preferred composition, namely sesame seed oil oxidized or treated with air in the presence of sulfur, with other triglycerides, or triglyceride containing oils, including corn oil, cottonseed oil, and triolein with regard to their respective peroxide titers indicates a trend in peroxide levels concordant with observed bioactivity in those having an addiction to tobacco. Such trend of bioactivity agrees in general with the results of a peroxide analysis involving the above-identified oils in their untreated state and when oxidized in the presence of elemental sulfur under similar conditions as follows:

| Oil Used (Peroxide Analysis) | PEROXIDE ANALYSIS (meq/kg.) | | |
|---|---|---|---|
| | "A" Oil Saturated With Sulfur | "B" Oil Treated* with Sulfur and Air | Δ = "B − A" Difference In Peroxide |
| Sesame Seed (10.2) | 18.8 | 35.7 | 16.9 |
| Corn (6.8) | 11.3 | 14.9 | 3.6 |
| Cottonseed (7.3) | 10.9 | 10.2 | −0.7** |
| Olive (5.9) | 12.4 | 13.8 | 1.4 |
| Triolein | 8.6 | 8.5 | −0.1** |

| Oil Used (Peroxide Analysis) | PEROXIDE ANALYSIS (meq/kg.) | | |
|---|---|---|---|
| | "A" Oil Saturated With Sulfur | "B" Oil Treated* with Sulfur and Air | Δ = "B − A" Difference In Peroxide |
| (7.2) | | | |

*Heated at 127° C. for 0.50 hrs. with 90 l/min. air addition and rapid mechanical stirring and containing 1.0% elemental sulfur by weight.
**Within experimental error.

It is thought that a lower bioactivity and a lower peroxide titer of cottonseed oil is due to the presence of natural anti-oxidants. The elimination of the anti-oxidants from oils such as corn and cottonseed oil or the use of the relatively pure allylically unsaturated compounds or mixtures thereof will produce a substantially increased peroxide titer when treated according to this invention. Triolein contains only oleic acid moieties which are characterized by the allylically unsaturated group —CH=CH—CH$_2$— and hence is quite difficult to oxidize,* particularly when compared to the preferred sesame seed oil. A peroxide titer value of 35.7 meq/kg. has been attained for the sesame seed oil-sulfur-oxygen treated composition while sesame seed oil oxidized alone at 137° C. yields a value of 63.3 meq/kg. a peroxide titer value of 35.7 meq/kg [Δ=(35.7−18.8)=16.91] has been attained for the sesame seed oil—sulfur—oxygen treated composition while sesame seed oil without sulfur oxidized at 137° C. yields a value of 63.3 meq/kg [Δ=(63.3−10.2)=53.1].
*J. Sci Fd. Agric. 1975, 26, 1353−1356.

Generally a substantial increase in the peroxide titer value can be defined as Δ3 to about Δ100 in cases where sulfur is incorporated into the composition and an from about Δ3 to about Δ400 when the oil is oxidized alone, or in the absence of sulfur.

The process used for determining the peroxide titer values discussed and reported herein are determined by placing a 2 gr. sample of the composition in a flask purged with nitrogen, and adding thereto 2 ml. of concentrated acetic acid and 0.5 grams of KI. The mixture is capped to exclude air and allowed to remain in the dark for 30 minutes to complete the reaction. The side walls are then wet down with a minimum of water and approximately 1-2 ml of a 2% starch added thereto. The solution is then immediately titrated to the end point with 0.007 normal Na$_2$S$_2$O$_2$ solution. The end point is white when small amounts of peroxides are present and slightly when larger amounts are present.

The compositions as prepared according to the process of this invention should be used soon after preparation as there is indication that the peroxide titer values and effectiveness of the compositions decrease upon aging.

Preferred compositions according to this invention can be prepared by adding the sulfur to the oil, such as sesame oil, and heating the mixture with agitation at a temperature not to exceed about 130° C. It is preferable or advantageous to heat the mixture between 120° and 127° C. Heating the mixture above about 130° C. for a sufficient time causes a progressive color change in the mixture and otherwise appears to be detrimental. The temperatures given above relate to the use of sulfur with sesame oil. The ranges of temperatures which can be used to produce the compositions made according to this invention may vary with the particular oil being used, but generally a temperature of 120° C., preferably 125° C. to 127° C., will be sufficient for most oils when sulfur is added.

If the oil and sulfur is heated below about 90° C., it is difficult to incorporate the sulfur into the oil by heating and stirring means. The best results have been obtained to date by maintaining the temperature used in forming the compositions over a prolonged period of time from about 30 minutes to one hour. Stirring aids in the reaction, and experiments to date indicate that a fairly violent stirring is advantageous. The introduction of air into the mixture during the heating is also very advantageous, particularly when the mixture is not subjected to prolonged heating and is the preferred method. The stirring can be accomplished with the introduction of the air.

After the reaction has taken place, it is cooled. Sulfur crystals remaining in the bottom of the reaction vessel can easily be removed by filtration. The remaining fluid is ready for use after appropriate sterilization for injection or incorporated into capsules, such as gelatin, for oral administration.

The amount of sulfur incorporated into the oil is advantageously between about 0.1% to 2.5% by weight, based on the oil. If higher amounts of sulfur are used they generally precipitate out. There appears to be no advantage to using higher amounts of sulfur in any event since the ultimate dosage given to the patient is the criteria rather than the amount of sulfur content in the oil.

As can be observed from Example 2 below, the incorporation of the sulfur into the oil seems to be limited to about 1% by the process presently being used to produce the sulfurized unsaturated oils.

The sulfur content can be much less than about 1% if desired and smaller sulfur content is advantageous when administered by injection. Varying the amount of sulfur below about 1% incorporated in the polyunsaturated oils for oral administration only affects the number of capsules to be taken at a given time by a particular patient.

Experiments to date indicate that the optimum sulfur content for oral administrations is about 1% and by injection about 0.1% to 0.3% by weight of the sulfur based on the weight of the oil.

The dosage prescribed to a patient will, of course, vary depending upon the particular patient and the number of cigarettes being smoked a day. In general, a daily dose of 3-5 capsules containing 1 ml of the sulfurized oil for the first three days after which the dose is progressively reduced. For example, for a heavy smoker it is advantageous for the patient to take about 8 capsules containing 1 ml of the sulfurized oil containing about 1% sulfur for the first three days and take 3 or 4 capsules a day for the next four days. This is generally sufficient to eliminate or reduce the desire or need for tobacco. The desire or need for tobacco generally disappears from the patient within 2-3 days. This single treatment may last for months. However, the patient can be given an additional supply of the encapsulated sulfurized oil and directed to take additional capsules if he feeds any desire or need for tobacco.

When the sulfurized oil is used by injection, such as intramuscularly or intraperitoneally, it is advantageous to have the sulfur contained in the sulfurized oil below about 0.5% by weight, preferably between about 0.1% to 0.3% by weight, and to inject from ½ to 3 ml of this solution into the patient. Experiments to date indicate that the injection of sulfurized oil is somewhat painful when it contains above about 0.3% sulfur. Administration by injection is, of course, not necessary, but it may act faster initially. Generally if a person is given the injection of the sulfurized oil, he can also be given a supply of the oral capsules and directed to take 3 to 4 capsules a day following the injection for one week.

EXAMPLE 1

A sulfurized oil was prepared by mixing 50 grams of sublimed sulfur, obtained from Fisher Scientific, with one liter of sesame oil. The mixture was heated under fairly rapid agitation by air to a temperature of about 127° C. until all of the sulfur was incorporated into the sesame oil. The reaction mixture was then cooled to room temperature, producing at the bottom of the reaction vessel a small amount of sulfur crystals. The crystals were then separated from the liquid by filtration and about half of the crystals replaced in the resulting liquid, wherein they slowly dissolved.

The resulting sulfurized oil was then incorporated into gelatin capsules in the amount of 1 ml per capsule.

Four patients reported that they had been smoking three to four packs of cigarettes a day. The patients were given 5 of the above capsules the first day and directed to take 5 capsules on the second and third days and 3 capsules for each of the four days remaining in the week. The patients reported no strong desire for tobacco after the third day and reduced their smoking habits to three to four cigarettes a day without nervousness or withdrawal symptoms.

Another patient who was smoking 60-80 cigarettes a day for the last 20 years was given 8 capsules of 1 ml of 1% sulfur in oil for three days. She remained without discomfort during this period. The treatment lasted 10 days with progressive reduced doses. The patient did not smoke for four months without the need for desire for smoking tobacco.

A number of other persons who were chronic smokers of varying degrees were also given the same dosage. Over all, based on the total number of persons so treated about 80% had an almost immediate loss of the desire to smoke while about 50% of the remaining persons felt a considerable loss of the desire to smoke after some time had passed while continuing the treatment. The remaining persons apparently did not lose their desire to smoke.

EXAMPLE 2

4 g. of sulfur were weighed out and placed in an Erlenmeyer flask. 200 ml of sesame oil were added; the contents were heated to 125° C. with stirring until the sulfur dissolved. The flask was removed from heat and allowed to cool to room temperature (5 hours). Sulfur crystals were filtered into a Buchner funnel, washed thoroughly with hexane to remove residual oil, and weighed.

The above example was repeated three times. The washed sulfur recipitated was weighed in each trial and the amount of sulfur in the sesame oil calculated by difference as follows:

| Initial weight of sulfur: 4.00 g | |
|---|---|
| Weight of sulfur ppt.: | |
| Trial 1 | 2.05 g |
| Trial 2 | 2.00 g |
| Trial 3 | 1.92 g |
| % (w/v) sulfur in sesame oil: | |

| Initial weight of sulfur: 4.00 g | |
|---|---|
| Trial 1 | 1.02% |
| Trial 2 | 1.00% |
| Trial 3 | 0.99% |
| Average | 0.99% |

From this it was concluded that the solutions contained approximately 1% sulfur after filtration.

The invention also includes the use of selenium in place of elemental sulfur and for the same use. When using selenium it is combined with the allylic moiety in the same manner as sulfur but heated to a temperature in the range of 230° to 250° C., preferably about 240° C. from 15 minutes to an hour or more or until the peroxide titer value is substantially greater than that of the untreated allylic moiety in the same manner as disclosed herein with respect to the use of sulfur. Those compositions into which selenium is incorporated have to date not indicated as good an effect as those composition into which sulfur is incorporated.

I claim:

1. A method for treating or aiding in the treatment of a tobacco habit or addiction in a human by controlling the craving for tobacco or controlling tobacco withdrawal symptoms, which comprises internally administering to said human an amount effective to control said craving or said withdrawal symptoms of an oxidized, sulfurized oil, produced by the process comprising heating in the presence of oxygen and elemental sulfur and at a temperature of from about 120° C. to about 130° C., an oil comprising at least one fatty acid or fatty ester having allylic unsaturation of at least one of the types

—CH=CH—CH₂—CH=CH— or

—CH=CH—CH=CH—CH₂— for a period of time sufficient to produce a peroxide titer substantially greater than the peroxide titer of said oil prior to oxidation.

2. The method of claim 1, wherein said oil is an animal, vegetable, or fish oil.

3. The method of claim 2, wherein the heating time is from about one half hour to about one hour.

4. The method of claim 1, wherein air or oxygen is injected into the oil during the heating thereof.

5. The method of claim 4, wherein the heating time is from about 0.5 to about 1 hour.

6. The method of claim 1, wherein the oil is a vegetable oil.

7. The method of claim 1, wherein the oil is sesame oil.

8. The method of claim 5, wherein the oil is a vegetable oil.

9. The method of claim 5, wherein the oil is sesame oil.

10. The method of claim 5, wherein the sulfur content of the resultant oxidized, sulfurized oil is from about 0.1% to about 2.5% by weight.

11. The method of claim 10, wherein the oxidized sulfurized oil is administered orally.

12. The method of claim 11, wherein the oil is sesame oil.

13. The method of claim 1, wherein the sulfur content of the resultant, oxidized, sulfurized oil is about 0.1% to about 0.3% by weight, and the oxidized sulfurized oil is administered intramuscularly or intraperitoneally.

14. The method of claim 13, wherein the oil is a vegetable oil.

15. The method of claim 13, wherein the oil is sesame oil.

* * * * *